United States Patent
Taylor

[19]

[11] Patent Number: 6,010,431
[45] Date of Patent: Jan. 4, 2000

[54] HAND STRETCHING METHOD FOR PREVENTING AND TREATING REPETITIVE STRESS INJURY

[76] Inventor: Donald N. Taylor, 4728 Rubes Creek Ct., Marietta, Ga. 30060

[21] Appl. No.: 09/274,029

[22] Filed: Mar. 22, 1999

Related U.S. Application Data

[62] Division of application No. 08/938,014, Sep. 13, 1997.

[51] Int. Cl.[7] ................................................... A63B 23/16
[52] U.S. Cl. .......................... 482/44; 482/91; 482/122; 482/128; 482/907; 601/40; 128/898
[58] Field of Search .................. 482/44, 91, 92, 482/907, 121, 122, 124, 128, 129, 139, 148; 601/23, 33, 40; 606/237, 241; 128/845, 898; 602/64

[56] References Cited

U.S. PATENT DOCUMENTS

| | | | |
|---|---|---|---|
| 3,924,283 | 12/1975 | Shave | 5/636 |
| 5,256,136 | 10/1993 | Sucher | 602/21 |
| 5,366,436 | 11/1994 | Gibney | 482/44 |
| 5,426,798 | 6/1995 | Guarino | 5/461 |
| 5,501,657 | 3/1996 | Feero | 601/40 |
| 5,529,550 | 6/1996 | Maycock, Jr. et al. | 482/44 |
| 5,642,543 | 7/1997 | Huntley | 5/640 |
| 5,769,758 | 6/1998 | Sarkinen | 482/44 |

Primary Examiner—Richard J. Apley
Assistant Examiner—Victor Hwang
Attorney, Agent, or Firm—James B. Middleton; Walter A. Rodgers

[57] ABSTRACT

A hand stretching method and apparatus mimics a well known exercise to reduce the problems with repetitive stress injury. A body of resiliently deformable material has flat and parallel top and bottom surfaces, with a cutout at one edge of the body. A user's hand is placed on the body, with the palm of the hand spanning the cutout. By pushing down on the hand, the opposite sides of the palm are urged apart, opening the carpal tunnel and relieving compression on the blood vessels and nerves. A user may place one hand on each surface of the body and urge the hands towards each other for treatment of both hands simultaneously. The body is preferably made of an expanded polymeric material such as polyurethane. Layers having different compression factors may be utilized; and, darker colored surface layers of material may be adhered to the top and bottom surfaces so the surfaces will not readily show dirt.

2 Claims, 1 Drawing Sheet

HAND STRETCHING METHOD FOR PREVENTING AND TREATING REPETITIVE STRESS INJURY

CROSS REFERENCE TO RELATED APPLICATION

This application is a division of the application by the same inventor, filed Sep. 13, 1997, under application Ser. No. 08/938014.

BACKGROUND OF THE INVENTION

1. Field of the Invention

This invention relates generally to exercising, and is more particularly concerned with a method and apparatus for exercising or stretching the hand for prevention and treatment of repetitive stress injury.

2. Discussion of the Prior Art

It is well known that a person who performs repetitive motions with his hands might develop a repetitive stress injury. Repetitive stress injury is also known synonymously as Occupational Overuse Syndrome, Cumulative Trauma Syndrome, and other names. These general disorders lead to more specific injury such as Tenosynovitis, Tendonitis, Carpal Tunnel Syndrome, Adverse Mechanical Tension and other conditions. The various problems are thought to be caused and/or aggravated by reduced blood flow to the hands. The reduced blood flow is often caused and/or aggravated by fatigued, tensed and/or swollen muscles and tendons which restrict the blood vessels and compress the median nerve in the wrist.

The prior art prescription for both prevention and treatment of repetitive stress injuries generally includes an exercising and/or stretching of the hand or wrist. One representative patent disclosing a treatment device is the patent to Sucher, U.S. Pat. No. 5,256,136. The Sucher device comprises a glove-like member that includes a platform to receive the palm of the hand. The platform has sectors that slope upwardly away from the palm area. The portion of the platform that receives the heel of the hand defines a recess so that, when the hand is urged down against the platform, the heel of the hand tends to bend, to spread the carpal tunnel. Without the use of an appliance of the Sucher type, it has been recommended that one simply press one's hands down against a flat surface. If another person is available to assist, the other person can manually bend and stretch the heel of the patient's hand in an effort to relax and stretch the muscles, and open the carpal tunnel. The Sucher device utilizes a generally hard surface, though a somewhat shaped surface, but the prior art has not provided a simple device to be used alone to accomplish the stretching of the heel of the hand for prevention or relief of a repetitive stress injury.

SUMMARY OF THE INVENTION

The present invention comprises a resiliently deformable body having opposed flat, parallel surfaces defining the top and bottom of the body. A cutout extends from the top to the bottom surface. The top and bottom surfaces of the body are of a size to receive a user's hand with fingers spread; and, the cutout is located and sized to engage opposite edges of the heel of the hand. The body has sufficient resistance to deformation that the user cannot bring the top and bottom surfaces together during normal use of the device.

In the preferred embodiment of the invention, the device is formed of a foamed elastomeric material, and the top and bottom surfaces are shaped to provide cues as to proper use of the device so a novice user will receive maximum benefit.

The method of the present invention comprises the steps of placing one's hand on the body of the device, with the heel of the hand spanning the cutout. One then pushes against the body, causing the fingers to be stretched backwards, and causing the heel of the hand to be stretched, pushing the two sides of the palm towards the back of the hand. Thus, the present invention mimics the treatment wherein another person manually stretches the heel of the hand.

BRIEF DESCRIPTION OF THE DRAWINGS

These and other features and advantages of the present invention will become apparent from consideration of the following specification when taken in conjunction with the accompanying drawings in which.

DETAILED DESCRIPTION OF THE EMBODIMENTS

Figure 1:
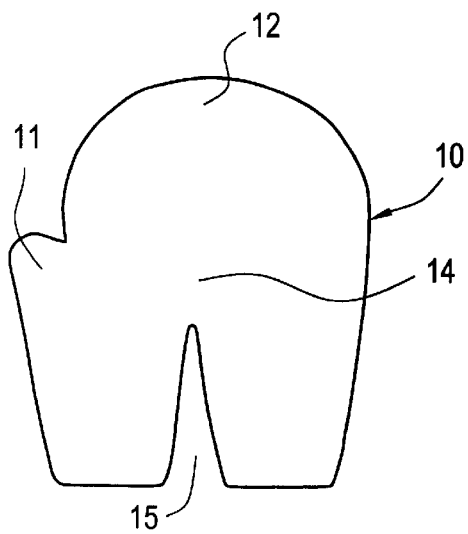
FIG. 1 is a top plan view of a hand stretching device made in accordance with the present invention.

Referring now more particularly to the drawings, and to those embodiments of the invention here presented by way of illustration, FIG. 1 is a top plan view of a stretching device comprising a body 10 shaped generally like an oven mitt. Thus the body 10 includes a thumb area 11 and a wide finger area 12. The palm of the hand will engage the central area 14 of the body 10; and, it will be noticed that a cutout 15 is defined in the edge of the body 10 opposite from the finger area 12.

Figure 2:
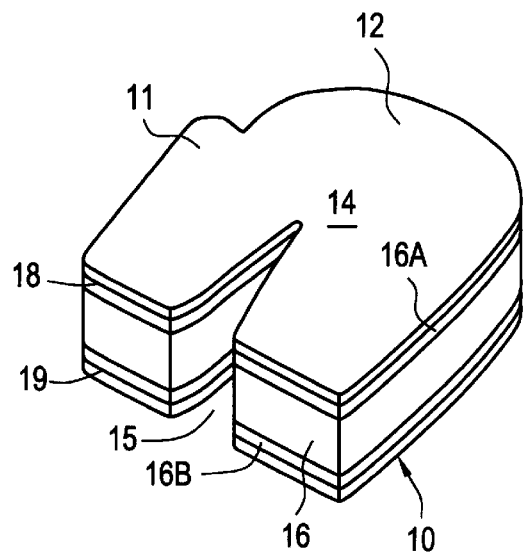
FIG. 2 is a perspective view of the device shown in FIG. 1.

Looking also at FIG. 2 of the drawings, it will be understood that the top and bottom surfaces of the body 10 are flat, and parallel to each other. As shown in FIG. 2, the top and bottom surface layers 18 and 19 are fixed to the body 10. It is contemplated that the surface layers 18 and 19 will be relatively thin, perhaps around one-fourth inch, or one-half centimeter. Those skilled in the art will understand that these dimensions are quite variable.

FIG. 2 also illustrates a plurality of layers of material to make up the body 10. The central layer is designated at 16, and upper and lower layers are designated at 16A and 16B. In such an arrangement it is contemplated that the central layer 16 may have a relatively high compression rating, while the upper and lower layers 16A and 16B will have a lower compression rating.

It will be understood that some people will prefer a softer feel to the device, while other people will prefer a harder feel. By utilizing the multiple layers, the initial feel will be relatively soft; and, after some compression, the feel will be harder. Thus, the layered device should appeal to a wide variety of people.

Figure 3:
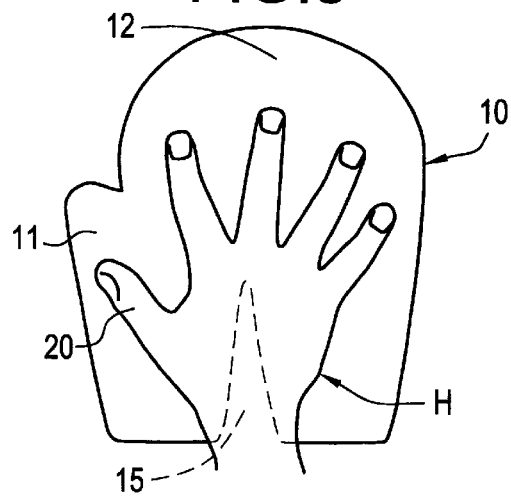
FIG. 3 is a view similar to FIG. 1 but showing a hand in position to utilize the device; and, FIGS. 4–6 are top plan views showing modifications of the device shown in FIGS. 1–3.

With attention to FIG. 3 of the drawings, it will be seen that a hand H is in position on the upper surface of the body 10 with the fingers spread apart. It will also be seen that the thumb area 11 is not shaped precisely to receive the thumb 20; rather, the thumb area 11 is simply a cue for the user to determine where his thumb goes on the device. Similarly, the finger area 12 is shaped to be a cue for placement of the fingers of the user as shown.

When the hand H is appropriately placed as shown in FIG. 3, the palm of the hand, hence the heel of the hand, straddles the cutout 15. As a result, if the hand is urged forcefully against the surface of the device, the opposite sides of the hand will tend to bend away from each other towards the back of the hand.

The body 10 of the present invention is made of a resiliently deformable material. One successful embodiment has been made of an expanded polyurethane, but numerous other materials may be equally successful. Generally any rubber or rubber-like material may be used, whether natural or synthetic. Thus, a natural latex or a synthetic latex can be used, or a polyvinyl chloride, ethylene vinyl acetate, urethane or virtually any other elastomeric material. The material is not necessarily foamed, or expanded, so long as the material is resiliently deformable with the force exerted by the user of the device of the present invention.

With the foregoing description in mind, use of the device of the present invention should be understandable. The user may place one hand against the device as shown in FIG. 3, the device resting on a flat surface. The user would then push down, against the body 10. Since the body 10 is resiliently deformable, the central portion 14 will be pushed down most because it receives the greatest force. The finger area 12 will be pushed down less because the fingers cannot exert a great enough force; therefore, the fingers will be bent back somewhat, as will the thumb 20. At the cutout 15, the body 10 will be pushed down on both sides of the cutout 15; but, farther from the cutout 15, the material will be deformed less because of the bulk of the body. As a result, the parts of the hand on opposite sides of the cutout 15 will be somewhat urged apart, and bent towards the back of the hand. The harder one pushes, the greater will be the resilient force stretching the hand.

An alternative method for using the device of the present invention is to place one hand on each of the top and bottom surfaces of the body 10. The user's hands are then urged towards each other as in an isometric exercise. As the resilient body 10 is compressed, the ameliorative forces will be exerted on both hands in the manner described above for one hand.

From the above description it will be understood that the physical attributes of the body 10 can vary rather widely. Thus, by way of example only, one successful embodiment of the invention has been made of an expanded polyurethane having a density of 1.8 pounds per cubic foot, and a compression of 60 pounds. The compression is measured by the standard test wherein a piece of foam 24 by 24 inches, by 4 inches, is compressed by a weight 24 by 24 inches, a distance of 25% of the thickness of the foam. This is referred to as the ILD 25% rating. The central portion 16 is 5 inches thick, and the upper and lower surface layers 18 and 19 are one-fourth inch thick. The overall dimensions are about 10½ inches long by 9 inches wide. The cutout 15 extends about one-third of the total length.

Again, the above specifications are by way of example only. The compression rating may be from about 20 pounds to about 90 pounds. The principal features are that there must be a resilient force urging the hand to bend backwards, and the user's force must not cause the upper surface to meet the lower surface. The density of the material is of little importance and could extend quite widely. The dimensions of the device must be such as to receive the hand of the user, and the size is otherwise of little importance. The upper and lower surface layers 18 and 19 may be omitted, but are included in the one embodiment for cosmetic purposes only. The body 10 is made of light-colored material that would quickly show dirt from use of the device. Thus, the surface layers 18 and 19 are of a dark gray or other dark color so dirt will not be really apparent after use of the device. Obviously the layers 18 and 19 may be sheet material that is not foamed, if desired.

Figure 4:
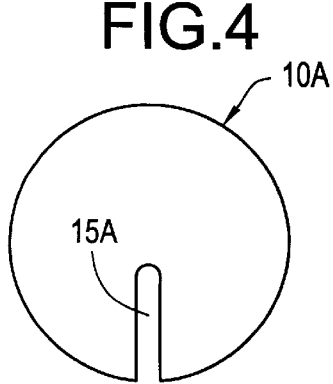
Figure 5:
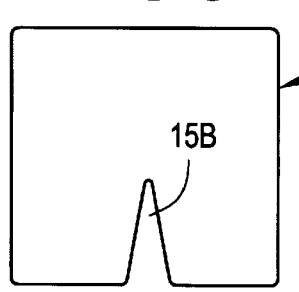
Figure 6:
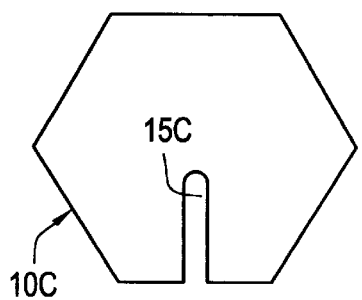

As is mentioned above, the shape of the body 10 is designed to provide cues as to proper hand placement on the body 10. Such cues may not be necessary; instead, one can be instructed in proper use. As a result, other shapes as shown in FIGS. 4–6, can be used. The drawings illustrate a circle, a rectangle and a hexagon, the bodies being designated as 10A, 10B and 10C respectively. FIGS. 4 and 6 further illustrate cutouts 15A and 15C that are not wedge-shaped. These and other body shapes may be used as desired and the results will be the same, so long as the hand is properly placed on the device.

It will therefore be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

What is claimed as invention is:

1. A method for preventing and treating repetitive stress injury comprising the steps of placing a hand on a surface of a resiliently deformable body, said body having a cutout therein, said step of placing a hand on said body including the step of placing the palm of the hand to span said cutout, and subsequently pushing down with said hand to compress said body, so that said resiliently deformable body urges opposite sides of said palm of said hand in opposite directions towards the back of the hand.

2. A method as claimed in claim 1, and further including the step of placing a first hand on the top surface of said body, placing the other hand on the bottom surface of said body, and urging said first hand and said other hand towards each other, so that said resiliently deformable body urges opposite sides of said palm of each hand in opposite directions towards the back of each respective hand.

\* \* \* \* \*